US00PP14787P3

(12) United States Plant Patent
VanLaeken

(10) Patent No.: US PP14,787 P3
(45) Date of Patent: May 18, 2004

(54) CLEMATIS PLANT NAMED 'SPRINKLES'

(50) Latin Name: *Clematis*
Varietal Denomination: Sprinkles

(76) Inventor: James P. VanLaeken, P.O. Box 552, Walworth, NY (US) 14568

( * ) Notice: Subject to any disclaimer, the term of this patent is extended or adjusted under 35 U.S.C. 154(b) by 4 days.

(21) Appl. No.: 09/964,948

(22) Filed: Sep. 27, 2001

(65) Prior Publication Data

US 2003/0061646 P1 Mar. 27, 2003

(51) Int. Cl.[7] ..... A01H 5/00
(52) U.S. Cl. ..... Plt./228

(58) Field of Search ..... Plt./228

(56) References Cited

PUBLICATIONS

Spring Valley Greenhouse, Inc. Catalogue (4th ed) p. 9 "Ernest Markham".

*Primary Examiner*—Kent Bell
(74) *Attorney, Agent, or Firm*—Fred L. Denson

(57) ABSTRACT

A new variety of clematis plant named 'Sprinkles'. The variety is characterized by wavy edged petals having sprinkles of light pink distributed throughout the tepal surface and a light pink bar that extends along the center longitudinal axis of each tepal.

1 Drawing Sheet

Botanical classification: Clematis.
Cultivar designation: 'Sprinkles'.

BACKGROUND OF THE NEW VARIETY

The present invention relates to a new and distinct cultivar of clematis species plant, hereinafter referred to by the name 'Sprinkles' (i.e. Genus Clematis, cultivar 'Sprinkles', species name unknown).

The new variety was discovered in a controlled planting of cultivated plants in a clematis nursery in Walworth, N.Y. in 1994. Plants were asexually propagated and observed over the next four years. In 1998, an offspring was selected and planted in an outside garden area and observed over the next two years. Propagation was done in Walworth, N.Y. Asexual propagation by vegetative cuttings has shown that the propagules are identical to the original plant in all distinguishing characteristics. The stability of the variety is evidenced by the distinguishing characteristics remaining true to form from generation to generation. The parentage of the variety is unknown; therefore, a species name is not designated.

SUMMARY OF THE INVENTION

Among the features which distinguish the new variety from other presently available and known commercial clematis cultivars are the unique color of the flower and the long blooming habit of the plant. The flower has sprinkles of light pink which are distributed throughout the tepals. A tepal typically carries a light pink bar that extends along its center longitudinal axis. While the light pink bar is not dominant or very pronounced or consistent throughout the flowers, it is consistent throughout the plant itself. However, the light pink bar may appear to be near white when contrasted against the rose pink color of the tepal edge. Their wavy edged tepals and rose-tipped stamens further distinguish the flowers.

RELEVANT PRIOR ART

The new variety is somewhat similar in appearance to the Ernest Markham variety as shown in the Spring Valley Greenhouse, Inc. catalogue ($4^{th}$ Edition) at page 9. While the flowers of both varieties are about the same size and have wavy edged tepals, there is a marked difference in the coloration of the tepals. The tepals of the Ernest Markham variety are a solid, magenta-red (PANTONE® #512C), whereas the tepals of the new variety have edges which are rose pink (PANTONE® #246U) and which fade to light pink in the center thereby forming a light pink bar in the middle of the tepal. Moreover, light pink is also sprinkled throughout the tepals creating an aesthetically soft appearance.

BRIEF DESCRIPTION OF THE PHOTOGRAPH

The accompanying photograph illustrates the overall appearance of the new variety. The flower and foliage colors as shown are, within the limitations of color photography, accurate and true reproductions of the actual colors of the new variety. The photographic view is a front elevation of typical Clematis Sprinkles in full bloom.

BOTANICAL DESCRIPTION

The following information is based on a six year old plant grown in Walworth, N.Y. Color refrences are based on using the PANTONE® matching system.

I. Plant:

*A. Form.*—Upright climbing or spreading.

*B. Growth.*—Vigorous, vining. 1. Height: approximately 10 feet to 12 feet. 2. Diameter/Spread: approximately 3 feet to 4 feet.

*C. Foliage.*—Deciduous, compound-trifoliate, opposite. 1. Size typical and observed: a. compound leaf length 2.5 inches, width 4.25 inches. b. individual leaflets length 1.75 inches, width 1 inch. c. simple leaf length 3 inches, width 2 inches. 2. Quantity per stem: typical and observed about 60. 3. Color: a. upper surface: dark green (PANTONE® #371C). b. lower surface: medium green (PANTONE® #377U). 4. Shape: lower leaves sometimes simple; normally three ovate leaflets in pinnate form; each leaf is cordate shaped. a. leaf base, typical and observed: rounded. b. leaf apex, typical and observed: acute. c. leaf edge, typical and observed: margin is entire. 5. Texture: upperside-glabrous veined, underside-ribbed 6. Petiole: a. color: green/red (PANTONE® #384U). b. length, typical and observed: 2 inches. c. diameter, typical and observed: 1/16 inch.

D. *Wood.*—1. New shoots. a. Color: light green (PANTONE® #582U). b. Bark: smooth. c. Internodes: cylindrical, approximately from about 5 inches to about 8 inches in length and 3/32 inch in diameter. 2. Old Wood. a. Color: light brown (PANTONE® #154C). b. Bark: rough.

E. *Hardiness.*—Zones 4 through 8.

F. *Disease.*—a. subject to any disease that normally affects clematis. b. has shown resistance to powdery mildew.

*G. Pests.*—a. subject to any pests that normally affect clematis.

II. Flower:

*A. Blooming habit.*—Recurrent, June to September based on climate in Rochester, N.Y. area.

*B. Bud.*—1. Size: typical and observed from about 1.5 inches to about 2.0 inches in length and about 5/8 inch in diameter. 2. Form: elliptic to ovate. 3. Color: green/grayish white (PANTONE® #435C).

*C. Stem.*—1. Length: from about 6 inches to about 8 inches. 2. Aspect: vertical. 3. Strength: erect. 4. Color: green (PANTONE® #582U), turning red/purple (PANTONE® #476C) with age.

*D. Bloom.*—1. Size, typical and observed: from about 4 inches to about 6 inches in diameter with a depth of 0.5 inch. 2. Form: round, very symmetrical with six (6) tepals of equal size overlapping with wavy margins. 3. Color upper surface: edges of tepals are rose pink (PANTONE® #246U) fading to light pink (PANTONE® #250C) in the center; this color (PANTONE® #250C) is also sprinkled throughout the tepals giving the plant a very soft look to the human eye. 4. Color lower surface: (PANTONE® #248U) fading to center color (PANTONE® #243U). 5. Characteristics: borne on 6 inch to 8 inch stems; suitable for cut flower arrangements. 6. Quantity: very floriferous, resulting from multiple buds formed on each stem, the typical and observed number of blooms per stem being from about 7 to about 10, and the typical and observed number of stems per plant being from about 50 to about 75. 7. Lastingness: about 7 to about 10 days as a cut flower and about 10 days to about 14 days on the plant.

*E. Tepals.*—1. Form: obovate in shape, starting 1/4 inch wide at its base, expanding halfway up to 1½ inches at its widest point and then tapering down to a pointed apex, the typical and observed overall tepal length being about 2¾ inches. 2. Arrangement: regularly arranged, slightly overlapping at base. 3. Fragrance: none. 4. Color: (see II D 3 and II D 4 above). 5. Margins, typical and observed: wavy, irregular. 6. Base, typical and observed: narrow.

III. Reproductive organs:

*A. Stamens, filaments and anthers.*—1. Arrangement: regularly arranged. 2. Stamens: typical and observed, 85 to 100 per bloom, (PANTONE® #461C), length 5/8 inch. 3. Anther: (PANTONE® #469C), length 3/16 inch. 4. Pistil: typical and observed from about 35 to about 50 per bloom, ½ inch in length.

*B. Pollen.*—1. Color: off white (PANTONE® #468C). 2. Amount: scarce.

*C. Styles.*—Bunched, even, average length.

*D. Stigmas.*—1. Color: off white (PANTONE® #461C).

*E. Seed, typical and observed.*—1. Diameter: 3/16 inch. 2. Thickness: 1/16 inch. 3. Color: (PANTONE® #145U). 4. Shape: spherical. 5. Quantity per bloom: 10 to 20. 6. Description: 1 inch to about 1½ inches in length, persistent style which is clothed with silky hairs 1/16 inch in length.

I claim:

1. A new and distinct variety of clematis plant named 'Sprinkles' as shown and described herein.

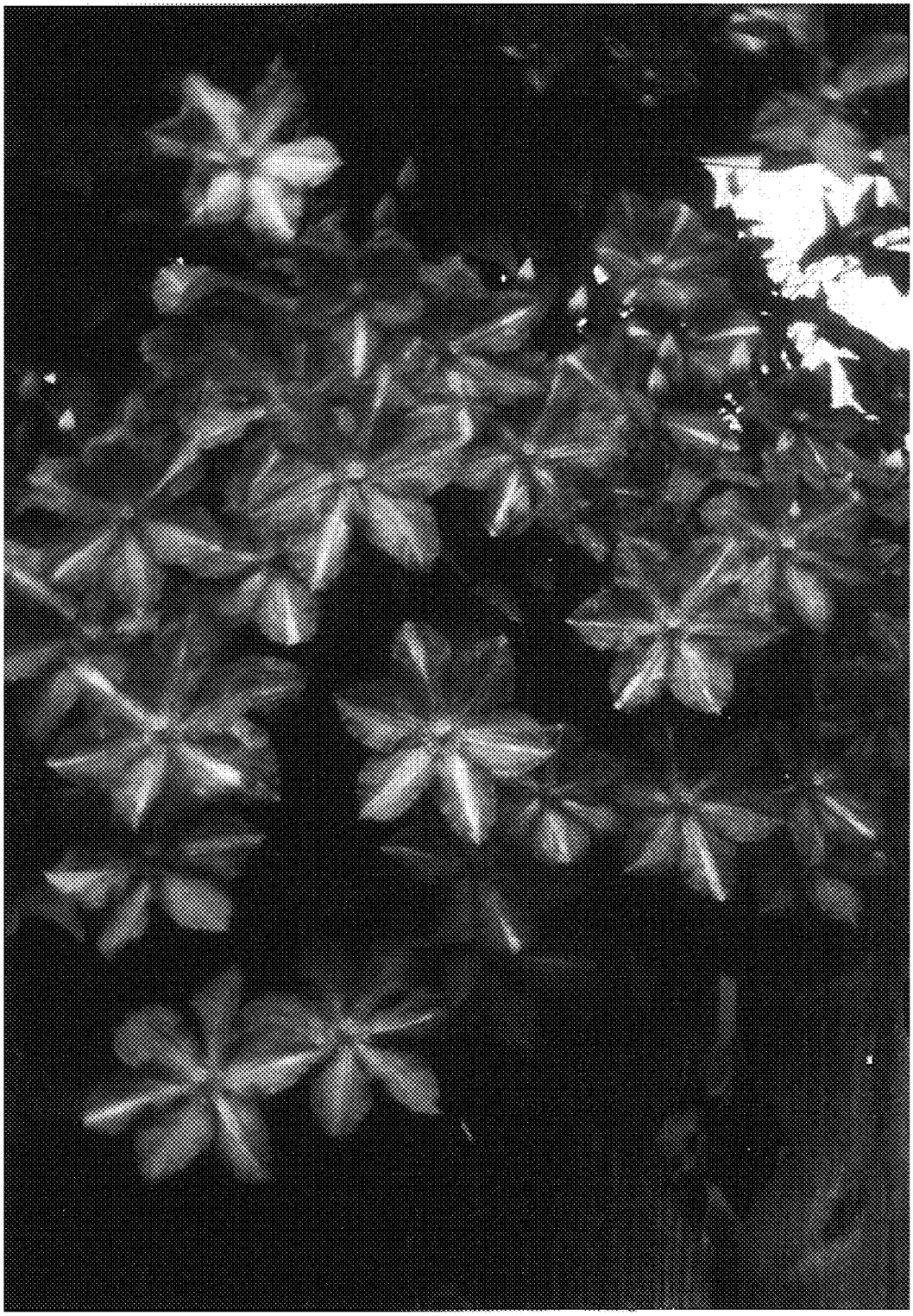

* * * * *